US009090855B2

(12) United States Patent
Polzin et al.

(10) Patent No.: US 9,090,855 B2
(45) Date of Patent: Jul. 28, 2015

(54) ANTI-BACTERIAL CLEANING COMPOSITION

(75) Inventors: Thomas E. Polzin, Sturtevant, WI (US); Lynn M. Werkowski, Oak Creek, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 13/156,379

(22) Filed: Jun. 9, 2011

(65) Prior Publication Data

US 2011/0311600 A1    Dec. 22, 2011

Related U.S. Application Data

(60) Provisional application No. 61/344,238, filed on Jun. 17, 2010.

(51) Int. Cl.
| | | |
|---|---|---|
| *A01N 33/12* | (2006.01) | |
| *A01P 1/00* | (2006.01) | |
| *A01N 25/30* | (2006.01) | |
| *C11D 3/20* | (2006.01) | |
| *C11D 1/66* | (2006.01) | |
| *C11D 1/835* | (2006.01) | |
| *C11D 3/30* | (2006.01) | |
| *C11D 3/48* | (2006.01) | |
| *C11D 1/62* | (2006.01) | |

(52) U.S. Cl.
CPC .............. *C11D 3/2068* (2013.01); *A01N 33/12* (2013.01); *C11D 1/66* (2013.01); *C11D 1/835* (2013.01); *C11D 3/2006* (2013.01); *C11D 3/2041* (2013.01); *C11D 3/30* (2013.01); *C11D 3/48* (2013.01); *C11D 1/62* (2013.01)

(58) Field of Classification Search
CPC ....................................................... A01N 33/12
See application file for complete search history.

(56) References Cited

U.S. PATENT DOCUMENTS

| | | | |
|---|---|---|---|
| 3,882,038 A | 5/1975 | Clayton et al. | |
| 4,315,828 A | 2/1982 | Church | |
| 5,290,472 A | 3/1994 | Michael | |
| 5,468,423 A | 11/1995 | Garabedian, Jr. et al. | |
| 5,507,971 A | 4/1996 | Ouzounis et al. | |
| 5,849,681 A | 12/1998 | Neumiller et al. | |
| 5,922,665 A | 7/1999 | Liu | |
| 6,090,771 A | 7/2000 | Burt et al. | |
| 6,376,448 B1 * | 4/2002 | Colurciello et al. | 510/384 |
| 6,683,036 B2 | 1/2004 | Foley et al. | |
| 6,730,654 B2 * | 5/2004 | Godfroid et al. | 510/499 |
| 6,849,589 B2 | 2/2005 | Liu | |
| 6,881,711 B1 | 4/2005 | Gershun et al. | |
| 6,936,580 B2 * | 8/2005 | Sherry et al. | 510/438 |
| 7,470,656 B2 | 12/2008 | Sherry et al. | |
| 2002/0103098 A1 * | 8/2002 | Harrison et al. | 510/382 |
| 2003/0064910 A1 | 4/2003 | Fong et al. | |
| 2003/0114342 A1 | 6/2003 | Hall | |
| 2005/0227897 A1 | 10/2005 | Nelson et al. | |
| 2008/0010772 A1 | 1/2008 | Kong et al. | |
| 2008/0275113 A1 | 11/2008 | Huetter et al. | |
| 2009/0311195 A1 | 12/2009 | Clark et al. | |
| 2009/0312228 A1 | 12/2009 | Bocage et al. | |
| 2010/0222248 A1 | 9/2010 | Komp et al. | |
| 2010/0240563 A1 * | 9/2010 | Jaynes et al. | 510/180 |

FOREIGN PATENT DOCUMENTS

GB          2340504 A       2/2000

OTHER PUBLICATIONS

TERGITOL® 15-S-9 Technical Data Sheet by Dow (retreived online Jan. 10, 2012 http://liveweb.archive.org/http://msdssearch.dow.com/PublishedLiteratureDOWCOM/dh_00ae/0901b803800aea3b.pdf?filepath=surfactants/pdfs/noreg/119-01950.pdf&fromPage=GetDoc.*
TERGITOL® Technical Data Sheet by Dow (published online by DOW on Feb. 21, 2008).*
Phyto Technology Laboratories (2004). http://parallax.sci.csupomona.edu/MSDS/PDP%20Files/White%20Distilled%20Vinegar%20MSDS.pdf.*
PCT/US2011/001076 International Search Report dated Oct. 12, 2011.

* cited by examiner

*Primary Examiner* — Scott Long
*Assistant Examiner* — Sarah Alawadi

(57) ABSTRACT

The present invention is directed to a multi-surface cleaning composition having an anti-bacterial ingredient for cleaning furniture surfaces. The anti-bacterial cleaning component includes a quaternary ammonium chloride compound or combinations thereof. The composition further includes a pH adjuster to provide for a generally neutral pH in the range of about 6 to about 9 including a combination of components, preferably white distilled vinegar and an amine compound. The cleaning composition provides for good cleaning and disinfecting of wood surfaces and other furniture surfaces without leaving streaks.

18 Claims, No Drawings

# ANTI-BACTERIAL CLEANING COMPOSITION

RELATED APPLICATION

The present application claims benefit of U.S. Provisional Application Ser. No. 61/344,238 filed Jun. 17, 2010 entitled "ANTI-BACTERIAL CLEANING COMPOSITION".

FIELD OF INVENTION

This invention relates to anti-bacterial cleaning compositions for use on furniture surfaces. More particularly, the invention relates to anti-bacterial cleaning compositions for use on multiple types of furniture surfaces, including on wood surfaces and glass surfaces, and provides good cleaning and disinfecting results without streaking.

BACKGROUND OF INVENTION

Multi-surface anti-bacterial cleaning compositions are known in the art. However, most of these cleaning compositions have a harsh pH, either very high or very low, and therefore are not conducive to cleaning furniture, especially wood furniture.

Multi-surface anti-bacterial cleaning compositions generally are required to have low volatile organic compound ("VOC") content, e.g. less than 3%. The formulation of low VOC content multi-surface anti-bacterial cleaning compositions is rendered difficult as the composition must meet the low VOC content requirement and at the same time provide for the optimum cleaning and disinfecting of the furniture surface, as well as not damage the surface being treated.

The present invention provides a new and useful anti-bacterial cleaning composition overcoming the problems of the prior art compositions.

SUMMARY OF INVENTION

The anti-bacterial cleaning composition of the present invention is useful for cleaning different furniture surfaces including wood, wood laminates and combination of wood and glass furniture. Additionally, the composition is useful for cleaning other furniture surfaces including marble, granite and stainless steel. The cleaning composition provides for beneficial cleaning of furniture due to the use of an anti-bacterial compound and having an adjusted pH in the range of about 6 to 9, more preferably 7 to 9, and most preferably 8 to 9. The pH is adjusted by a combination of ingredients, including the use of white distilled vinegar and an amine. The adjusted pH renders the composition less harsh and allows for the safe and effective cleaning and disinfecting of furniture surfaces, especially wood and wood laminate surfaces.

The cleaning composition of the invention includes an anti-bacterial ingredient to provide for a generally microbial-free surface. The anti-bacterial ingredient useful in the invention is a quaternary ammonium chloride or combinations thereof.

The cleaning composition of the invention further provides for a low degree of foaming, thereby reducing streaking of the furniture and glass surfaces. The low degree of foaming in the composition is achieved by, among other things, the use of a nonionic surfactant. Use of a nonionic surfactant without an anionic or amphoteric surfactant functions well with the quaternary ammonium chloride active cleaning ingredient.

The cleaning composition of the present invention is preferably used in an aerosol delivery system. However, the composition also may be delivered by a trigger spray container or impregnated into a wipe.

DETAILED DESCRIPTION OF THE INVENTION

The present invention is directed to a multi-surface cleaning composition having an anti-bacterial ingredient for cleaning furniture surfaces. The anti-bacterial cleaning component comprises a quaternary ammonium chloride compound. The composition further includes a pH adjuster to provide for a generally neutral pH in the range of about 6 to about 9, more preferably 7 to 9, and most preferably 8 to 9, comprising a combination of components, preferably white distilled vinegar and an amine compound. The cleaning composition provides for good cleaning and disinfecting of wood surfaces and other furniture surfaces, including entertainment centers having a combination of wood and glass surfaces. The cleaning composition does so without leaving streaks on the furniture surface.

The anti-bacterial/disinfectant cleaning component is a quaternary ammonium chloride. This component provides for the effective killing of microbial elements. The quaternary ammonium chloride component may be one or a combination of quaternary ammonium chloride compounds. A preferred quaternary ammonium chloride is a combination of an alkyl dimethyl benzyl ammonium chloride and an alkyl dimethyl ethylbenzyl ammonium chloride. Presently preferred quaternary ammonium chlorides include BTC 2125M manufactured and sold by Stepan Company and BARQUAT 4280-Z manufactured and sold by Lonza, Inc. These are long chain (i.e., $C_{12}$-$C_{18}$) quaternary ammonium chlorides and combine well with the nonionic surfactant as discussed hereafter. The anti-bacterial agent may be present in the range (by weight %) of about 0.001 to about 0.25%. A more preferred range is about 0.005 to about 0.15%. The most preferred range is about 0.01 to about 0.1%.

The cleaning composition includes a pH adjuster to provide a pH in the range of about 6 to about 9. This pH range provides for the good cleaning of furniture, including wood surfaces, without damaging such surfaces which is not possible with the known anti-bacterial hard surface cleaning compositions which generally have a harsh pH, e.g. either in the range of around 3 on the acidic side or in the range of 10 to 11 on the alkaline side. The pH boosters useful in the composition are water-soluble organic and/or inorganic builders. Preferably, the pH boosters comprise white distilled vinegar, i.e. acetic acid (15% active) and an amine. The white distilled vinegar generally provides for a pH in the range of 5 to 6 when used with the additional components of the composition. The pH is further adjusted to the range of about 8 to about 9 with the use of an amine, preferably an alkanolamine, more preferably ethanolamine. The amine provides for adjustment of the pH and also functions as a cleaning agent. The pH boosters may be present in the range (by weight %) of about 0.001 to about 2.0%. A preferred range is about 0.05 to about 1.0%. The most preferred range is about 0.2 to about 0.6%.

The composition further includes a nonionic and/or cationic surfactant which works well with the quaternary ammonium chloride. The preferred non-ionic surfactant is an alkoxylated linear alcohol. Preferred surfactants are secondary alcohol alkoxylates, in particular ethoxylates, such as Tergitol 15-S-9 manufactured and sold by The Dow Chemical Company which is a $C_6$-$C_{17}$ secondary alcohol poly (3-6 EO) ethoxylate. Additional nonionic surfactants useful with the invention include alkanolamides, amine oxides, and ethoxylated fatty esters. These nonionic surfactants have a low level of foaming when combined with the other ingredients of the composition providing for good cleaning, removal of microbial elements and avoidance of streaking of the furniture surface. The surfactant may be present in the range (by weight %) of about 0.001 to about 0.5%. The preferred range is about 0.01 to about 0.2%. The most preferred range is about 0.04 to about 0.12%.

The cleaning composition does not use amphoteric or anionic surfactants. These surfactants will bind with the quaternary ammonium chloride, thereby reducing the effectiveness of the anti-bacterial agent due to decreasing the level of actives available. Additionally, such surfactants may increase the level of foaming which is not desirable.

The cleaning composition of the invention further includes water-soluble solvents and/or solublizers which include water, glycols, glycol ethers and alcohols. The preferred solvents include short carbon chain alkylene glycols, alkylene glycol ethers and alkanols; and most preferably ethylene glycol n-hexyl ether, propylene glycol and isopropanol. The solvents and/or solublizer are present in the range (by weight %) of about 95.0 to about 99.8%. The preferred range is about 97.5 to about 99.8%. The most preferred range is about 98.5 to about 99.8%.

A fragrance is preferably included in the composition. A presently preferred fragrance is a citrus fragrance which conveys freshness and cleanliness to the user. The fragrance is present in the range (by weight %) of about 0.001 to about 1.0%. The preferred range is about 0.01 to about 0.8%. The most preferred range is about 0.05 to about 0.4%.

The preferred delivery system for the cleaning composition of the invention is an aerosol delivery system. The aerosol delivery system preferred is compressed gas, and more preferably compressed air or nitrogen. However, a hydrocarbon gas aerosol is also suitable for use. The cleaning composition of the invention may also use a trigger (non-aerosol) delivery system or be impregnated in a wipe.

In one presently preferred embodiment of the invention, a useful anti-bacterial cleaning composition for cleaning furniture comprises:

| Ingredient | Wt. % |
|---|---|
| Water (Diluent) | 96.614 |
| Isopropanol (Solvent) | 1.5 |
| Compressed Air or Nitrogen (Propellant) | 0.8 |
| Ethylene Glycol n-Hexyl Ether (Solvent) (aka Hexyl Cellosolve) | 0.3 |
| White Distilled Vinegar (aka acetic acid, 15% active) (pH booster) | 0.3 |
| Fragrance Mixture | 0.15 |
| Propylene Glycol (Solvent) | 0.13 |
| Ethanolamine (pH Adjuster and Cleaning Agent) | 0.1 |
| TERGITOL 15-S-9 (Nonionic Surfactant) (Ethoxylated Linear Alcohol) (Secondary Alcohol Ethoxylate) (Alcohol $C_6$-$C_{17}$ (Secondary)poly(3-6)ethoxylate) | 0.075 |
| BTC 2125M (80% Actives); (Disinfectant) (n-alkyl dimethylbenzyl ammonium chloride/ n-alkyl dimethyl ethylbenzyl ammonium chloride) OR BARQUAT 4280-Z (80% Actives); (Disinfectant) (n-alkyl dimethylbenzyl ammonium chloride/ n-alkyl dimethyl ethylbenzyl ammonium chloride) | 0.031 |
| | 100% | pH = 8.5

While the above composition is a presently preferred embodiment of the invention, it is understood that different ranges of ingredients may be used, as well as different combinations of base ingredients or equivalents of base ingredients, including as set forth herein.

As will be apparent to one skilled in the art, various modifications can be made within the scope of the aforesaid description. Such modifications being within the ability of one skilled in the art form part of the present invention.

It is claimed:

1. Anti-bacterial cleaning composition for application on furniture surfaces to clean and disinfect such surfaces without streaking consisting of
    (a) about 0.001 to 0.25 wt. % of a quaternary ammonium chloride cleaning component;
    (b) about 0.05 to about 1 wt. % white distilled vinegar;
    (c) about 0.05 to about 1 wt. % alkanolamine;
    (d) about 95 to about 99.8 wt. % of a water-soluble solvent or solubilizer selected from the group consisting of water, alcohol, alkylene glycol ether, alkylene glycol, and mixtures thereof;
    (e) about 0.001 to about 0.5 wt. % of a nonionic surfactant selected from the group consisting of alkoxylated linear alcohol, alkanolamide, amine oxide, ethoxylated fatty ester, and mixtures thereof;
    (f) a fragrance component; and
    (g) a propellant;
wherein said composition has a pH of about 8 to about 9, and weight total of the composition is based on 100 wt. %.

2. The anti-bacterial cleaning composition of claim 1, wherein said nonionic surfactant is an alkoxylated linear alcohol.

3. The anti-bacterial cleaning composition of claim 2, wherein said alkoxylated linear alcohol is an ethoxylated linear alcohol.

4. The anti-bacterial cleaning composition of claim 3, wherein said ethoxylated linear alcohol is a $C_{6-17}$ ethoxylated linear alcohol with 3-6 ethylene oxide groups.

5. The anti-bacterial cleaning composition of claim 1, wherein said propellant is a compressed gas or a hydrocarbon.

6. The anti-bacterial cleaning composition of claim 1, wherein said water-soluble solvent or solubilizer is a mixture of water, an alcohol, an alkylene glycol ether, and alkylene glycol.

7. The anti-bacterial cleaning composition of claim 1, wherein said furniture surfaces include surfaces made of wood, wood laminate, combination of wood and glass, marble, granite, stainless steel, or combination thereof.

8. The anti-bacterial cleaning composition of claim 1, wherein
    (a) said quaternary ammonium chloride cleaning component is present in an amount of about 0.005 to about 0.15 wt. %;
    (b) said vinegar and said alkanolamine together are present in an amount of about 0.05 to about 1 wt. %;
    (c) said nonionic surfactant is present in an amount of about 0.01 to about 0.2 wt. %; and
    (d) said water-soluble solvent or solubilizer is present in an amount of about 97.5 to about 99.8 wt. %.

9. The anti-bacterial cleaning composition of claim 1, wherein
    (a) said quaternary ammonium chloride cleaning component is present in an amount of about 0.01 to about 0.1 wt. %;
    (b) said vinegar and said alkanolamine together are present in an amount of about 0.2 to about 0.6 wt. %;

(c) said nonionic surfactant is present in an amount of about 0.04 to about 0.12 wt. %; and
(d) said water-soluble solvent or solubilizer is present in an amount of about 98.5 to about 99.8 wt. %.

10. The anti-bacterial cleaning composition of claim 9, wherein said pH is about 8 to about 9.

11. Anti-bacterial cleaning composition for application on furniture surfaces to clean and disinfect such surfaces without streaking consisting of
(a) about 0.005 to 0.25 wt. % of an alkyl dimethyl benzyl ammonium chloride and an alkyl dimethyl alkylbenzyl ammonium chloride;
(b) white distilled vinegar and alkanolamine together are present in an amount of about 0.05 to about 1 wt. %;
(c) about 97.5 to about 99.8 wt. % of a water-soluble solvent or solubilizer selected from the group consisting of water, alcohol, alkylene glycol ether, alkylene glycol, and mixtures thereof;
(d) about 0.01 to about 0.2 wt. % of a nonionic surfactant selected from the group consisting of alkoxylated linear alcohol, alkanolamide, amine oxide, and ethoxylated fatty ester, and mixtures thereof;
(e) a fragrance component; and
(f) a propellant;
wherein said composition has a pH of about 7 to about 9, and weight total of the composition is based on 100 wt. %.

12. Anti-bacterial cleaning composition for application on furniture surfaces to clean and disinfect such surfaces without streaking consisting of
(a) about 0.001 to 0.25 wt. % of a quaternary ammonium chloride cleaning component;
(b) about 0.05 to about 1 wt. % white distilled vinegar;
(c) about 0.05 to about 1 wt. % alkanolamine;
(d) about 95 to about 99.8 wt. % of a water-soluble solvent or solubilizer selected from the group consisting of water, alcohol, alkylene glycol ether, alkylene glycol, and mixtures thereof;
(e) about 0.001 to about 0.5 wt. % of a nonionic surfactant selected from the group consisting of alkoxylated linear alcohol, alkanolamide, amine oxide, ethoxylated fatty ester, and mixtures thereof; and
(f) a fragrance component;
wherein said composition has a pH of about 8 to about 9, and weight total of the composition is based on 100 wt. %.

13. Anti-bacterial cleaning composition for application on furniture surfaces to clean and disinfect such surfaces without streaking consisting of
(a) about 0.001 to 0.25 wt. % of a quaternary ammonium chloride cleaning component;
(b) about 0.05 to about 1 wt. % white distilled vinegar;
(c) about 0.05 to about 1 wt. % alkanolamine;
(d) about 95 to about 99.8 wt. % of a water-soluble solvent or solubilizer selected from the group consisting of water, alcohol, alkylene glycol ether, alkylene glycol, and mixtures thereof;
(e) about 0.001 to about 0.5 wt. % of a nonionic surfactant selected from the group consisting of alkoxylated linear alcohol, alkanolamide, amine oxide, ethoxylated fatty ester, and mixtures thereof, wherein said nonionic surfactant is combined with a cationic surfactant;
(f) a fragrance component; and
(g) a propellant;
wherein said composition has a pH of about 8 to about 9, and weight total of the composition is based on 100 wt. %.

14. The anti-bacterial cleaning composition of claim 12, wherein said composition is impregnated in a wipe or dispensed from a trigger sprayer.

15. Anti-bacterial cleaning composition for application on furniture surfaces to clean and disinfect such surfaces without streaking consisting of
(a) about 0.001 to 0.25 wt. % of a quaternary ammonium chloride cleaning component;
(b) about 0.05 to about 1 wt. % white distilled vinegar;
(c) about 0.05 to about 1 wt. % alkanolamine;
(d) about 95 to about 99.8 wt. % of a water-soluble solvent or solubilizer selected from the group consisting of water, alcohol, alkylene glycol ether, alkylene glycol, and mixtures thereof;
(e) about 0.001 to about 0.5 wt. % of a nonionic surfactant selected from the group consisting of alkoxylated linear alcohol, alkanolamide, amine oxide, ethoxylated fatty ester, and mixtures thereof;
(f) a fragrance component;
(g) a colorant component; and
(h) a propellant;
wherein said composition has a pH of about 8 to about 9, and weight total of the composition is based on 100 wt. %.

16. Anti-bacterial cleaning composition for application on furniture surfaces to clean and disinfect such surfaces without streaking consisting of
(a) about 0.001 to 0.25 wt. % of a quaternary ammonium chloride cleaning component;
(b) about 0.05 to about 1 wt. % white distilled vinegar;
(c) about 0.05 to about 1 wt. % alkanolamine;
(d) about 95 to about 99.8 wt. % of a water-soluble solvent or solubilizer selected from the group consisting of water, alcohol, alkylene glycol ether, alkylene glycol, and mixtures thereof;
(e) about 0.001 to about 0.5 wt. % of a nonionic surfactant selected from the group consisting of alkoxylated linear alcohol, alkanolamide, amine oxide, ethoxylated fatty ester, and mixtures thereof; and
(f) a fragrance component;
(g) a colorant component;
wherein said composition has a pH of about 8 to about 9, and weight total of the composition is based on 100 wt. %.

17. Anti-bacterial cleaning composition for application on furniture surfaces to clean and disinfect such surfaces without streaking consisting of
(a) about 0.001 to 0.25 wt. % of a quaternary ammonium chloride cleaning component;
(b) about 0.05 to about 1 wt. % white distilled vinegar;
(c) about 0.05 to about 1 wt. % alkanolamine;
(d) about 95 to about 99.8 wt. % of a water-soluble solvent or solubilizer selected from the group consisting of water, alcohol, alkylene glycol ether, alkylene glycol, and mixtures thereof;
(e) about 0.001 to about 0.5 wt. % of a nonionic surfactant selected from the group consisting of alkoxylated linear alcohol, alkanolamide, amine oxide, ethoxylated fatty ester, and mixtures thereof, wherein said nonionic surfactant is combined with a cationic surfactant;
(f) a fragrance component;
(g) a colorant component; and
(h) a propellant;
wherein said composition has a pH of about 8 to about 9, and weight total of the composition is based on 100 wt. %.

18. Anti-bacterial cleaning composition for application on furniture surfaces to clean and disinfect such surfaces without streaking consisting of
(a) about 0.001 to 0.25 wt. % of a quaternary ammonium chloride cleaning component;
(b) about 0.05 to about 1 wt. % white distilled vinegar;
(c) about 0.05 to about 1 wt. % alkanolamine;

(d) about 95 to about 99.8 wt. % of a water-soluble solvent or solubilizer selected from the group consisting of water, alcohol, alkylene glycol ether, alkylene glycol, and mixtures thereof;
(e) about 0.001 to about 0.5 wt. % of a nonionic surfactant selected from the group consisting of alkoxylated linear alcohol, alkanolamide, amine oxide, ethoxylated fatty ester, and mixtures thereof, wherein said nonionic surfactant is combined with a cationic surfactant; and
(f) a fragrance component;
(g) a colorant component;
wherein said composition has a pH of about 8 to about 9, and weight total of the composition is based on 100 wt. %.

* * * * *